(12) United States Patent
Maev et al.

(10) Patent No.: US 9,296,062 B2
(45) Date of Patent: Mar. 29, 2016

(54) ULTRASONIC IN-PROCESS MONITORING AND FEEDBACK OF RESISTANCE SPOT WELD QUALITY

(71) Applicants: Roman Gr Maev, Windsor (CA); Andriy M Chertov, Windsor (CA); John M Paille, Rochester Hills, MI (US); Frank J Ewasyshyn, Rochester, MI (US)

(72) Inventors: Roman Gr Maev, Windsor (CA); Andriy M Chertov, Windsor (CA); John M Paille, Rochester Hills, MI (US); Frank J Ewasyshyn, Rochester, MI (US)

(73) Assignee: Tessonics Corporation, Birmingham, MI (US)

(*) Notice: Subject to any disclaimer, the term of this patent is extended or adjusted under 35 U.S.C. 154(b) by 0 days.

(21) Appl. No.: 13/913,772

(22) Filed: Jun. 10, 2013

(65) Prior Publication Data

US 2013/0269439 A1 Oct. 17, 2013

Related U.S. Application Data

(63) Continuation of application No. 11/221,545, filed on Sep. 8, 2005, now abandoned.

(60) Provisional application No. 60/614,572, filed on Sep. 30, 2004.

(51) Int. Cl.
| | |
|---|---|
| B23K 11/25 | (2006.01) |
| B23K 20/10 | (2006.01) |
| B23K 31/12 | (2006.01) |
| G01N 29/07 | (2006.01) |
| G01N 29/22 | (2006.01) |
| G01N 29/34 | (2006.01) |

(52) U.S. Cl.
CPC ............ *B23K 11/25* (2013.01); *B23K 11/252* (2013.01); *B23K 20/10* (2013.01); *B23K 31/12* (2013.01); *G01N 29/07* (2013.01); *G01N 29/223* (2013.01); *G01N 29/343* (2013.01); *G01N 2291/0251* (2013.01); *G01N 2291/02854* (2013.01); *G01N 2291/02863* (2013.01); *G01N 2291/044* (2013.01); *G01N 2291/0422* (2013.01); *G01N 2291/101* (2013.01); *G01N 2291/102* (2013.01); *G01N 2291/2672* (2013.01)

(58) Field of Classification Search
USPC ........ 219/109, 91.1, 110, 111, 117.1; 73/588, 73/599, 600, 602, 618
See application file for complete search history.

(56) References Cited

U.S. PATENT DOCUMENTS

| | | | | |
|---|---|---|---|---|
| 4,099,045 | A * | 7/1978 | Okuda et al. | 219/109 |
| 4,449,029 | A * | 5/1984 | Nied | 219/117.1 |
| 4,711,984 | A * | 12/1987 | Bilge et al. | 219/110 |
| 2003/0023393 | A1* | 1/2003 | Oravecz | 702/39 |

* cited by examiner

*Primary Examiner* — Brian Jennison
(74) *Attorney, Agent, or Firm* — Carlson, Gaskey & Olds P.C.

(57) ABSTRACT

A method and apparatus for ultrasonic in-process monitoring and feedback of resistance spot weld quality uses at least one transducer located in the electrode assembly transmitting through a weld tip into an underway weld. Analysis of the spectrum of ultrasonic waves provides the operator with an indication of the size, thickness, location, dynamics of formation and quality of the spot weld. The method presents a fundamentally new physical approach to the characterization of the spot weld quality. Together with transmission mode it includes new modes of operation of ultrasonic probes such as a reflection mode and simultaneous use of transmission and reflection modes, and a new physical interpretation of the signal analysis results.

4 Claims, 7 Drawing Sheets

ULTRASONIC IN-PROCESS MONITORING AND FEEDBACK OF RESISTANCE SPOT WELD QUALITY

CROSS-REFERENCE TO RELATED APPLICATIONS

This patent application is a continuation, claiming the benefit of U.S. Ser. No. 11/221,545, filed Sep. 8, 2005, which also claims the benefit of U.S. Provisional Ser. No. 60/614,572, filed Sep. 30, 2004.

BACKGROUND OF THE INVENTION

1. Field of the Invention

The present invention relates to an ultrasonic transducer associated with an electrode for real-time monitoring and feedback in a welding process.

2. Description of Related Art

The nondestructive testing of spot welds in real time using ultrasound has many advantages over other nondestructive approaches. Prior art arrangements include the insertion of the ultrasonic probe into the weld electrodes, with the acoustic energy sent through the weld subject. Then the analysis of the transmitted and/or reflected signal is performed in order to make some conclusions about the quality of the weld.

U.S. Pat. No. 3,726,130 discloses a probe glued to the back surface of the welding electrode. The probe generates a shear wave and receives a reflection from the primary solid-liquid interface of the weld. This method allows the determination of the penetration depth of the liquid zone into the subject. However, this method only gives information about one side of the weld, telling nothing about the opposite side. Also, as weld electrodes must be frequently changed or refreshed, this arrangement of the probe on the surface of the removable electrode can make it impractical or susceptible to damage in an industrial setting.

U.S. Pat. No. 4,099,045 discloses an acoustic wave undergoing multiple reflections within a weld subject. Evaluation of the degree of attenuation of the wave provides some information about the spot weld. This is an empirical approach which requires a collection of data for each particular case. The method enables prediction of the quality of the weld by comparison with previous results.

U.S. Pat. No. 6,297,467 discloses an electrode assembly incorporating ultrasonic probes and its basic principles of operation, and is hereby incorporated herein in its entirety.

It would be advantageous to provide a method of using acoustic waves to directly measure the dynamics of formation of weld and critical parameters which define the weld quality without comparing weld characteristics with previously tabulated results.

BRIEF SUMMARY OF THE INVENTION

In an embodiment of the present invention, a spot welder has either two electrode assemblies containing ultrasonic probes (for transmission mode or for combination of transmission and reflection modes) or just one electrode assembly (for purely reflection mode). During welding the ultrasonic probe from first electrode assembly generates a burst of acoustic energy. In transmission mode, one portion of this acoustic energy passes through a weld zone and then is picked up by the second probe located in the second electrode assembly. In reflection mode, another portion is reflected by the weld subject and is received by the first ultrasonic probe. The third option includes simultaneous operation of transmission and reflection modes. Both ultrasonic probes in the electrode assemblies then emit an output electrical signal to the computer. The computer processes the received signals and outputs the information about the weld geometry and the "time history" of the weld. This information is used by the computer software to make a decision whether it is necessary to change welding parameters in real time to provide the quality output. This comprises the feedback stage of ultrasonic in-process welding quality control.

BRIEF DESCRIPTION OF THE SEVERAL VIEWS OF THE DRAWINGS

The present invention will become more fully understood from the detailed description and the accompanying drawings, wherein.

DETAILED DESCRIPTION OF THE INVENTION

Figure 1:
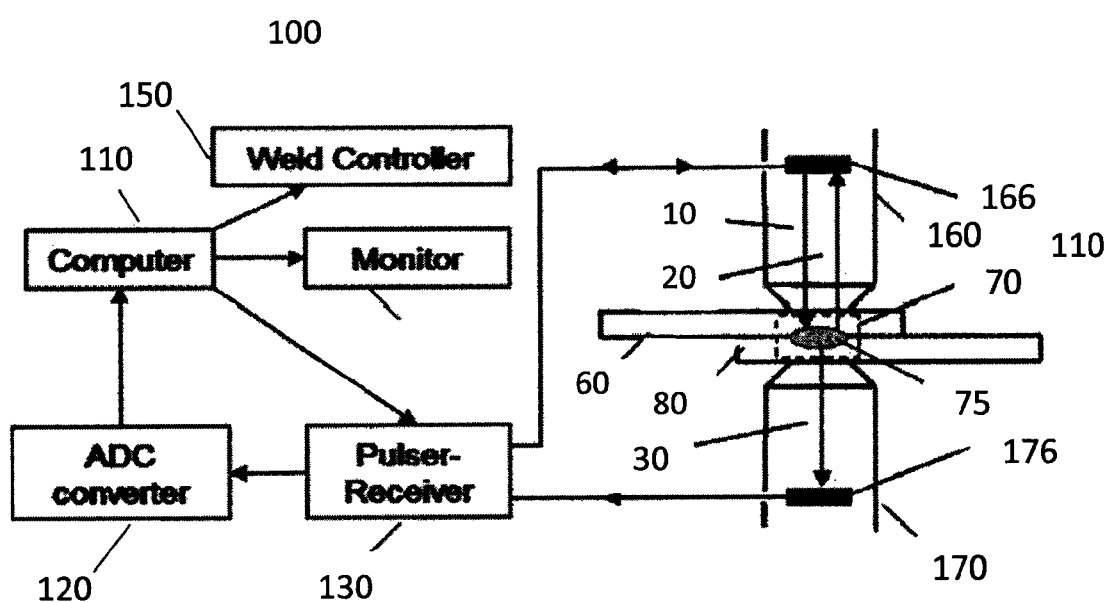
FIG. 1 is a schematic representation of an apparatus for ultrasonic in-process monitoring and feedback of resistance spot weld quality according to the invention.

Referring to FIG. 1, an apparatus 100 for ultrasonic in-process monitoring and feedback according to the invention includes a computer 110, analog-digital converter (ADC) 120, pulser-receiver 130, monitor 140, weld controller 150 and acoustic transmitter-receiver probes 166, 176 mounted within weld electrodes 160, 170.

Each of the electrodes 160, 170 includes a probe 166, 176 capable of emitting and receiving acoustic waves 10, 20 and 30. The computer 110 sends commands to the weld controller 150 and the pulser-receiver 130. The weld controller 150 clamps the electrodes 160, 170 and starts welding. Simultaneously, the pulser-receiver 130 sends electrical pulses to a probe 166 located in one of the electrodes. The electrical energy is converted into mechanical energy in the form of acoustic waves 10.

The waves 10 propagate through the first and second metal layers 60, 80 and the weld zone 70 as long as the metal is transparent to sound waves. The weld zone 70 includes a liquid metal zone and adjacent areas.

The probe 166 emits incident wave 10. Part of the wave 10 is reflected by the weld zone 70 and shown as reflected wave 20. Reflected wave 20 is received by the same probe 166, and received by the pulser-receiver 130. A portion of wave 10 shown as wave 30 passes through weld zone 70 and is picked up by probe 176. The received acoustic wave 30 is also sent to the pulser-receiver 130. Pulser-receiver 130 forwards the signals to the ADC 120. The digitized signal is sent to the computer 110 and processed with special signal processing software. The results of signal processing and signal analysis can be output to the monitor 140 or stored as a computer file.

Figure 2:
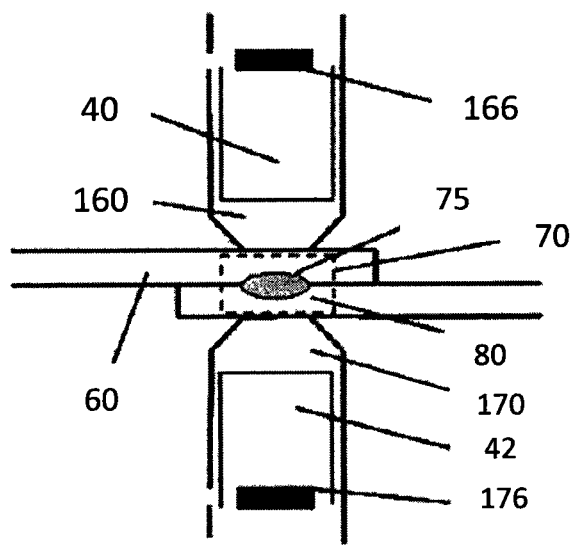
FIG. 2 is an enlarged view of an electrode assembly of FIG. 1.

Referring to the FIG. 2, the incident and reflected waves 10, 20 (shown in FIG. 1) pass through the several media. The incident wave 10, generated by the probe 166, propagates through a cooling water column 40 which works as a couplant for the acoustic waves. The wave 10 propagates through the body of the electrode 160 and enters the first metal sheet 60. Part of the wave 10, as wave 30, passes through the weld zone 70, body of the second electrode 170 and water column 42. The weld zone 70 is defined as a bulk volume of the welded metal sheets located between the tips of the two electrodes and the volume of the dynamic molten region including all interfaces between all substances in this zone. Then the wave 30 induces electrical signals in the piezoelectric crystal of the probe 176 that are returned to the pulser-receiver 130.

Figure 3:
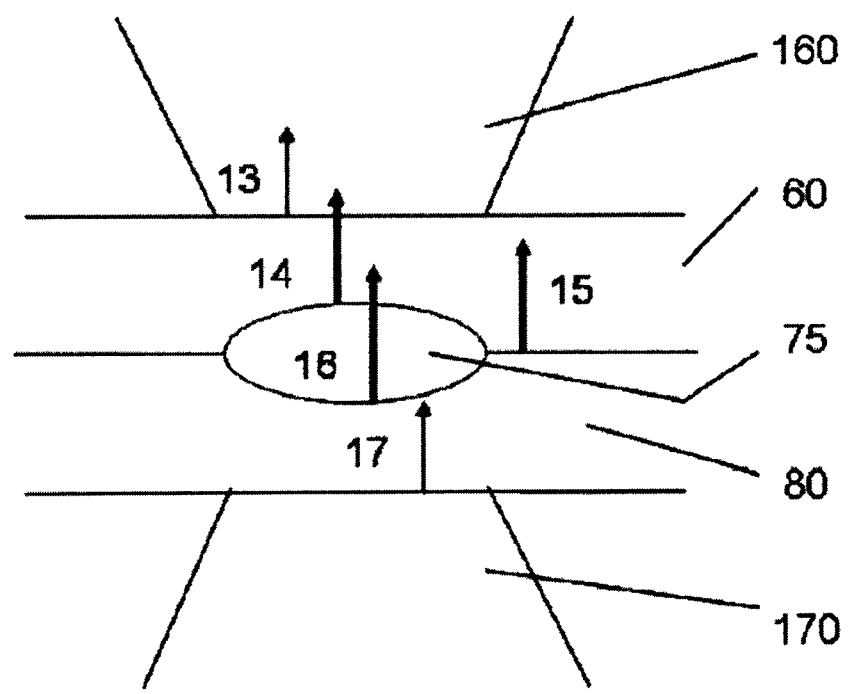
FIG. 3 is an enlarged representation of reflected waves within the weld zone of FIGS. 1-2.

Wave 20, a portion of the wave 10, reflects from the weld zone 70. Referring to FIG. 3, the incident wave 10 reflects from the interface of the electrode 160 and sheet-metal 60 as ray 13. The reflection of wave 10 from the interface of the first sheet-metal 60 and liquid zone 75 is shown as ray 14. The reflection from the interface of first sheet-metal 60 and second sheet-metal 80 is shown as ray 15. The reflection from the interface of liquid zone 75 and second sheet-metal is shown as ray 16. The reflection from the interface of second sheet-metal 80 and electrode 170 is shown as ray 17. All these reflected rays 13, 14, 15, 16, 17 come back to the probe 166 as reflected wave 20. Wave 20 generates the electrical signal in the piezoelectric crystal of the probe 166.

All of the received signals come to the pulser-receiver 130, and then are forwarded to the ADC 120 and then to the computer 110.

Figure 4:
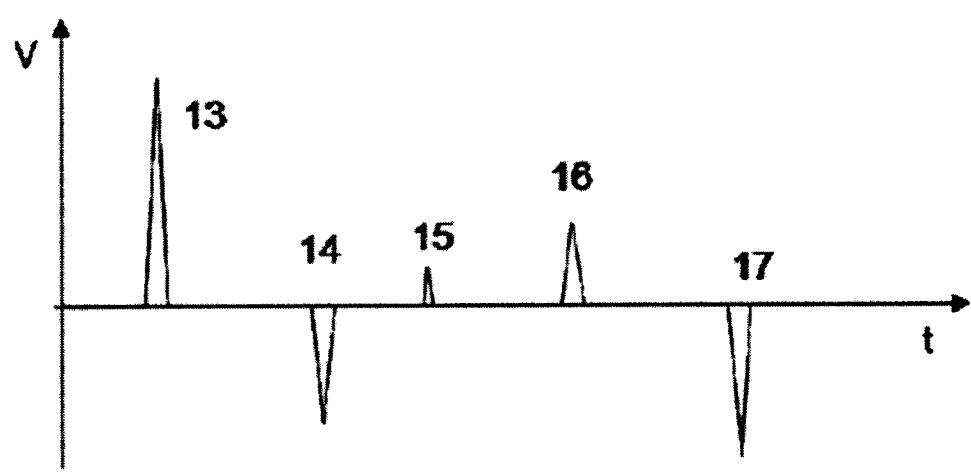
FIG. 4 is an oscillogram of reflected waves within the system of FIGS. 1-3.

FIG. 4 depicts an oscillogram of the reflected wave 20, showing each of the reflected components illustrated as rays 13, 14, 15, 16, 17. Using the oscillogram, it is possible to determine the geometry and position of the liquid portion of the weld zone 70 at given moment during welding. Signals 13 and 17 are used as the reference points to locate the position of the upper interface of the first plate and the lower interface of the second plate.

Signal 14 inverts its phase when the wave strikes solid-liquid interface. The impedance of the liquid is lower than that of the solid metal. Such kind of impedance mismatch gives rise to the phase inversion of the reflected signal 14.

Signal 16 is reflected from liquid-solid interface. Its phase is always inverted with respect to signal 14 because phase inversion happens only when impedance of second medium is less than that of the first.

Signal 15 comes from the interface of the two sheet-metals. The greater the lateral size of the molten region the weaker this signal is due to the reduced reflecting area within the range of the main lobe of the wave generated by the probe 166.

The phase inversion of the reflected signal is the crucial feature which allows say that one really deals with the solid-liquid interface and not with some artifact. Calculation of the distance between the reflected signal peaks 14 and 16, on the time scale t, provides information about the thickness of the liquid zone 75. The positioning, on the time scale t, of the peak 14 with respect to peak 13, and the peak 16 with respect to peak 17, gives an indication of the position of the liquid zone relative to the outer surfaces of the sheet-metal 60, 80. Position of the peaks 14, 16 with respect to peak 15 further provides an indication of the position of the liquid zone relative to the interface between sheet-metal 60, 80. This information is of particular importance in the welding of high strength steel, when position of the nugget is not symmetrical with respect to the central contact interface.

The comparison of the amplitude of peak 15 and peak 14 provides information about the lateral size of the liquid zone 75. The smaller the amplitude of peak 15 the bigger area is covered by the weld liquid zone 75 in lateral directions. Disappearance of the peak 15 indicates that the liquid zone 75 is equal to or bigger than the main lobe width of the incident wave 10. When the width of the main lobe is known, it is possible to calculate a minimum lateral size of the liquid zone 75 by evaluation of the amplitude of peaks 14, 15.

Figure 5:
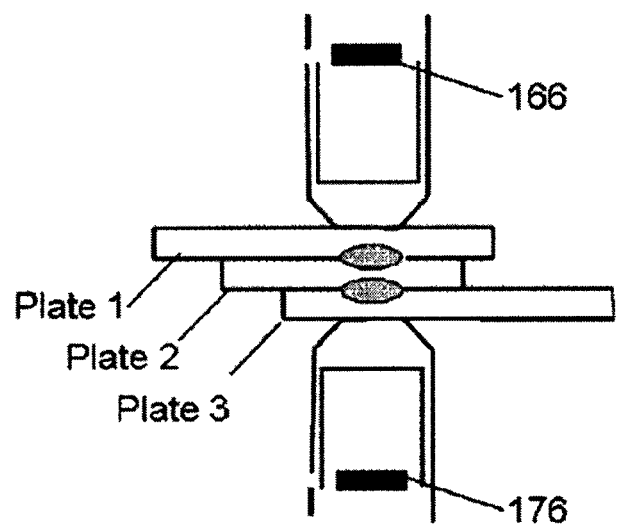
FIG. 5 is a side view of a three-layer weld subject.

A similar analysis can be applied to the composition of three and more sheets put together. An example of such an arrangement is shown in FIG. 5.

Specially designed signal processing software allows the removal of unwanted noise, helping to distinguish the reflections from all interfaces. With the waves 10 sent through the weld 70 during the whole process of welding, the resultant data stream illustrates the dynamic picture of liquid zone growth and its position with respect to the outer interfaces of the sheet-metal 60, 80.

Figure 6:
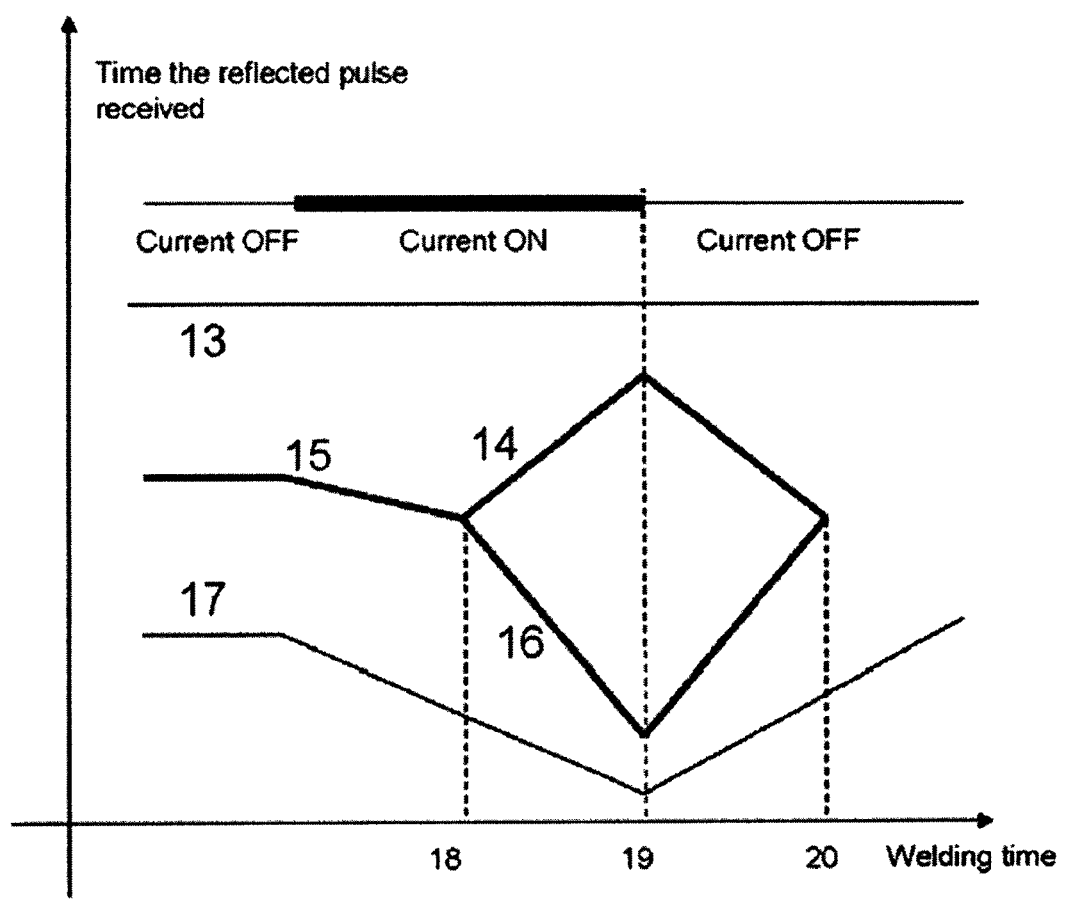
FIG. 6 is a dynamic graphing of the oscillograms representing the welding process.

Referring to FIG. 6, the arrival time of signals reflected from different interfaces at different moments of welding is presented. Before welding started, only signals 13, 15, 17 are visible. When welding starts, the velocity of wave propagation in the metal decreases. This leads to the increase of propagation time of the wave in the metal. When melting begins, two additional interfaces appear, a solid-liquid interface 14 and liquid-solid interface 16. The moment of appearance 18 of these signals is the moment of the beginning of melting of metal. The elapsed time from the moment of appearance 18 until the weld current is turned off at the moment 19 is the time of growth of the liquid zone.

After the current is turned off, the liquid zone shrinks until the sheet-metal has re-solidified. The weld nugget is formed in place of the liquid zone. The weld nugget is defined as the volume of metal which used to be liquid zone during welding. At the moment of re-solidification 20, the interfaces 14, 16 disappear. The elapsed time 19-20 is the solidification time, a further indicator of the weld nugget strength.

Figure 7:
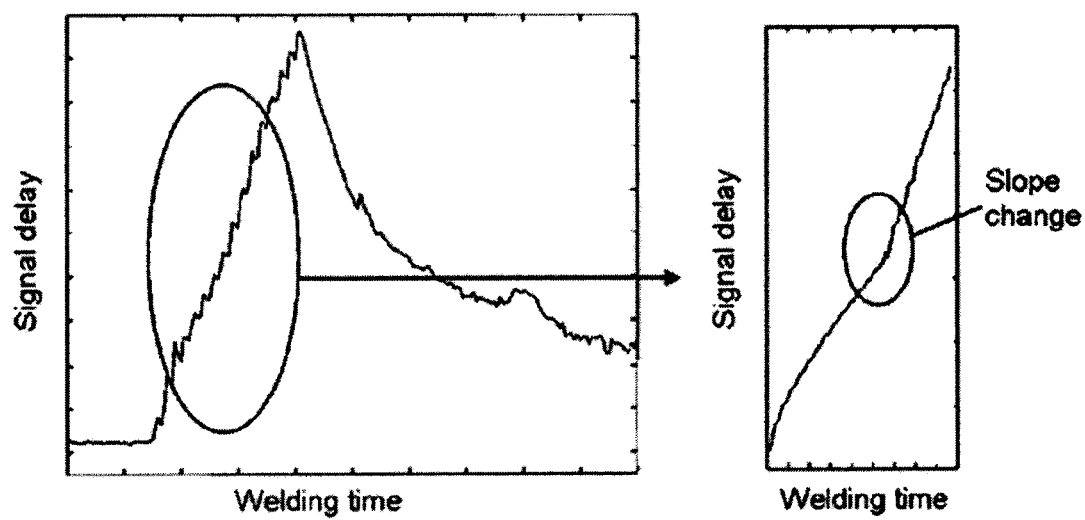
FIG. 7 is a pair of graphs showing a time of flight for good quality weld, comparing actual results with a model. A good weld is indicated by a change of slope highlighted by the circle on the right graph.

A further method of in-process monitoring is based on using the transmission mode and is characterized in FIG. 7. FIG. 7 the time of flight (TOF) of the series of signals 30 through the weld subject of FIG. 1. Referring to the FIG. 7, this delay is not linear throughout the welding process. As the material warms up, the sound velocity decreases through the material so that the delay of the transmitted signal increases. The melting of the liquid zone, the change in phase from solid to liquid, results in a discontinuous change of the physical properties of the material. These properties include resistivity and, notably, sound velocity, as is reflected in the discontinuity of the TOF graphs of FIG. 7.

This abrupt change of the properties can be monitored by measuring the delay of the wave passing through the weld before and after melting moment. The moment of the beginning of melting is seen on the time of flight curve shown on FIG. 7 as a change of the slope of the curve to the higher values. The abrupt increase of the signal delay at a certain moment of welding corresponds to the beginning of melting of the welded plates. The computer 110 determines the exact moment of the start of melting. The time from this moment up to the end of welding is the time of liquid pool growth. The time of liquid pool growth characterizes the weld nugget size. The computer 110 uses the time of the beginning of melting to instruct the weld controller 150 to discontinue the current at an appropriate time for adequate weld growth.

This time of flight (TOF) jump does not occur in a stick weld. In stick weld the mating surfaces are weakly bonded in the weld zone—when the sheets are peeled apart there is no nugget present. Thus this technique is capable of distinguishing stick weld from one in which the weld nugget has formed. It can also qualitatively characterize the weld by measuring the time between the start of melting and the moment the current is off. The through transmission mode distinguishes between a stick weld and a proper weld based on the exact duration of liquid zone growth.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the scope of the appended claims.

What is claimed is:

1. An apparatus for monitoring welding in a resistance welder, the resistance welder including first and second electrodes, the apparatus comprising:

an ultrasonic probe disposed within the first electrode that is capable of generating a burst of acoustic energy that is directed to a weld subject including at least two metal parts disposed between the first and second electrodes, the ultrasonic probe configured to receive reflected acoustic energy from the weld subject in response to the burst and to generate an output signal in response to the reflected acoustic energy, the reflected acoustic energy including a phase inverted acoustic wave reflected from an interface between a liquid zone and a solid portion of the metal part proximal to the ultrasonic probe, the reflected acoustic energy including a second acoustic wave reflected from an interface between the liquid zone and a solid portion of the metal part distal to the ultrasonic probe; and a computer configured to receive the output signal, the computer configured to monitor the output signal over time including monitoring the phase inverted acoustic wave over time while weld current is applied to determine a characteristic of the weld, the computer configured to monitor a change in time of flight of the acoustic energy through the weld subject and to monitor a change in slope of a curve of the change in time of flight to detect a beginning of melting of the weld subject.

2. The apparatus of claim 1 wherein the reflected acoustic energy includes a first acoustic wave having a first phase and the phase inverted acoustic wave is a succeeding acoustic wave having a second phase inverted from the first phase.

3. The apparatus of claim 2 wherein computer is configured to determine the presence of the liquid zone based upon the inversion of the second phase relative to the first phase.

4. The apparatus of claim 2 wherein the computer is configured to determine an initiation of the interface between the liquid zone and the solid portion of the metal, to monitor a thickness of the liquid zone over time and to monitor solidification of the liquid zone.

* * * * *